US008742174B2

(12) United States Patent
Mägerlein et al.

(10) Patent No.: US 8,742,174 B2
(45) Date of Patent: Jun. 3, 2014

(54) METHOD FOR PREPARING HIGHER ETHANOLAMINES

(75) Inventors: Wolfgang Mägerlein, Mannheim (DE); Johann-Peter Melder, Böhl-Iggelheim (DE); Jörg Pastre, Bensheim (DE); Jan Eberhardt, Mannheim (DE); Thomas Krug, Worms (DE); Mirko Kreitschmann, Mannheim (DE)

(73) Assignee: BASF SE, Ludwigshafen (DE)

( * ) Notice: Subject to any disclaimer, the term of this patent is extended or adjusted under 35 U.S.C. 154(b) by 33 days.

(21) Appl. No.: 13/516,521

(22) PCT Filed: Dec. 13, 2010

(86) PCT No.: PCT/EP2010/069467
§ 371 (c)(1),
(2), (4) Date: Jun. 15, 2012

(87) PCT Pub. No.: WO2011/082967
PCT Pub. Date: Jul. 14, 2011

(65) Prior Publication Data
US 2012/0259139 A1    Oct. 11, 2012

(30) Foreign Application Priority Data
Dec. 17, 2009  (EP) ..................... 09179708

(51) Int. Cl.
*C07C 209/26* (2006.01)
*C07C 209/28* (2006.01)

(52) U.S. Cl.
USPC ........................................ 564/473

(58) Field of Classification Search
USPC ........................................ 564/473
See application file for complete search history.

(56) References Cited

U.S. PATENT DOCUMENTS

| 4,264,776 | A |   | 4/1981  | Hershman et al. |
|-----------|---|---|---------|-----------------|
| 4,322,568 | A |   | 3/1982  | Weiss |
| 4,328,370 | A |   | 5/1982  | Fazio |
| 5,023,379 | A |   | 6/1991  | Felder et al. |
| 5,530,127 | A |   | 6/1996  | Reif et al. |
| 5,536,691 | A |   | 7/1996  | Breitscheidel et al. |
| 5,696,048 | A |   | 12/1997 | Breitscheidel et al. |
| 6,147,261 | A | * | 11/2000 | Knifton et al. ............... 564/473 |
| 2001/0003136 | A1 |  | 6/2001  | Nouwen et al. |
| 2002/0115890 | A1 |  | 8/2002  | Melder et al. |
| 2003/0065224 | A1 |  | 4/2003  | Peschel et al. |
| 2003/0149310 | A1 |  | 8/2003  | Gerlach et al. |
| 2007/0249871 | A1 |  | 10/2007 | Almeida Lenero et al. |
| 2008/0081931 | A1 |  | 4/2008  | Puckette et al. |
| 2009/0012333 | A1 |  | 1/2009  | Almeida Lenero et al. |
| 2012/0271068 | A1 |  | 10/2012 | Magerlein et al. |

FOREIGN PATENT DOCUMENTS

| CS | 8609428       |   | 9/1990  |             |
|----|---------------|---|---------|-------------|
| DE | 4400591 A1    |   | 7/1995  |             |
| DE | 10059629 A1   |   | 6/2002  |             |
| DE | 10143424 A1   |   | 3/2003  |             |
| EP | 0238961 A2    |   | 9/1987  |             |
| EP | 636409 A1     |   | 2/1995  |             |
| EP | 0663389       | * | 7/1995  | ... B01J 23/46 |
| EP | 696572 A1     |   | 2/1996  |             |
| EP | 742045 A1     |   | 11/1996 |             |
| EP | 963975 A1     |   | 12/1999 |             |
| EP | 1106600 A2    |   | 6/2001  |             |
| EP | 1317959 A1    |   | 6/2003  |             |
| EP | 1697291 A1    |   | 9/2006  |             |
| JP | 3246248 A     |   | 11/1991 |             |
| JP | 3279342 A     |   | 12/1991 |             |
| WO | WO-2011/082994 A1 | | 7/2011 |             |

OTHER PUBLICATIONS

Hall, A.W., et al., "Synthesis of Some [N-(2-Haloalkyl)amino]tetralin Derivatives as Potential Irreversible Labels for Bovine Anterior Pituitary $D_2$ Dopamine Receptors", J. Med. Chem., vol. 30, (1987), pp. 1879-1887.

Hrnciar, Peter, et al., "Synthesis of Novel Nocathiacin-Class Antibiotics. Condensation of Glycolaldehyde with Primary Amides and Tandem Reductive Amination of Amadori-Rearranged 2-Oxoethyl Intermediates", J. Org. Chem., vol. 67, (2002), pp. 8789-8793.

International Search Report for PCT/EP2010/069467 mailed Mar. 31, 2011.

English Translation of International Search Report for PCT/EP2010/0694467, dated Mar. 31, 2011.

English Translation of Written Opinion of International Searching Authority for PCT/EP2010/0694467, dated Jul. 3, 2012.

Kua, et al., "Glycoaldehyde Monomer and Oligomer Equilibria in Aqueous Solution: Comparing Computational Chemistry and NMR Data," 117 *J. Phys. Chem. A.* 2997, 2998 (2013).

* cited by examiner

*Primary Examiner* — Brian J Davis
(74) *Attorney, Agent, or Firm* — Drinker Biddle & Reath LLP

(57) ABSTRACT

The present invention relates to a process for preparing ethanolamines by reacting glycolaldehyde with monoethanolamine and/or diethanolamine in the presence of a catalyst.

13 Claims, No Drawings

METHOD FOR PREPARING HIGHER ETHANOLAMINES

RELATED APPLICATIONS

This application is a national stage application (under 35 U.S.C. §371) of PCT/EP2010/069467, filed Dec. 13, 2010, which claims benefit of European Patent Application No. 09179708.4, filed Dec. 17, 2009.

The present invention relates to the preparation of ethanolamines.

The preparation of ethanolamines is known from the prior art.

Ullmann's Enzyklopädie der technischen Chemie (chapter "Ethanolamine and Propanolamine" [Ethanolamines and propanolamines], Wiley-VCH, 2005) states that ethanolamines are prepared commercially exclusively by reaction of ethylene oxide with excess ammonia, and the preparation can typically be effected in the presence of water as a catalyst. The reaction product formed at first is monoethanolamine (MEOA), which reacts in a further reaction with further ethylene oxide to give diethanolamine (DEOA) and triethanolamine (TEOA). The reaction proceeds under kinetic control, i.e. the composition of the product mixture depends essentially on the molar ratio of the ammonia used to ethylene oxide.

Thus, higher ethanolamines, such as DEOA and TEOA, are obtained preferentially when the molar ratio of ammonia to ethylene oxide is less than 5:1. At the same time, the ratio of ammonia to ethylene oxide, as described in DE-A-10143424, should, however, not go below a value of 1.01:1, in order to ensure that the ethylene oxide used has reacted fully for safety reasons, since ethylene oxide can polymerize explosively in the presence of ammonia and amines. Even at a molar ratio of 1.01:1 to 5:1, in the case of preparation of the higher ethanolamines, such as DEOA and TEOA, MEOA always also forms as a coproduct, since all reaction steps have essentially the same activation energy and the same quadratic dependence of the reaction rate of water.

The reaction mixture obtained in the preparation is therefore generally separated by distillation in order to obtain the desired ethanolamines in pure form.

Since the ratio of the ethanolamines thus obtained does not always correspond to the ratio required by the market, the prior art therefore describes various processes which enable the conversion of ethanolamines.

For instance, U.S. Pat. No. 4,264,776 describes the catalytic oxidation of triethanolamine with oxygen to give diethanolamine in the presence of an activated carbon catalyst.

U.S. Pat. No. 4,328,370 discloses the conversion of lower trialkanolamines to mono- and dialkanolamines by reaction with ammonia at elevated temperature in the presence of a hydrogenation catalyst.

However, the conversion of MEOA to higher ethanolamines is not described.

DE-A-10059629 describes the conversion of an ethanolamine mixture with a particular composition to an ethanolamine mixture with a composition different than the original composition. For example, DEOA is obtained by reacting MEOA and TEOA, or TEOA and ammonia in the presence of a strong base. The yields of DEOA obtained by means of this process are generally less than 20% by weight.

However, the preparation of DEOA from MEOA always requires at least an equivalent amount of TEOA, such that it is not possible to increase the proportion of higher ethanolamines overall.

It was an object of the present invention to provide a process for preparing ethanolamines, which enables higher ethanolamines, such as DEOA and TEOA, to be synthesized in high yield and selectivity. More particularly, the process should be performable without ethylene oxide in order to avoid the safety complexity required in the case of use of ethylene oxide.

The object of the present invention is achieved by a process for preparing ethanolamines by reacting glycolaldehyde with monoethanolamine and/or diethanolamine in the presence of a catalyst.

The process according to the invention takes place in the presence of a catalyst.

The catalysts used may in principle be all catalysts which comprise nickel, cobalt, iron, copper, ruthenium, chromium, manganese, copper, molybdenum, tungsten, rhenium and/or other metals of groups 8 and/or 9 and/or 10 and/or 11 of the periodic table of the elements (Periodic Table in the IUPAC version dated Jun. 22, 2007).

Preference is given to using catalysts which comprise copper, cobalt and/or nickel.

The abovementioned catalysts can be doped in a customary manner with promoters, for example with chromium, iron, cobalt, manganese, molybdenum, titanium, tin, metals of the alkali metal group, metals of the alkaline earth metal group and/or phosphorus.

In a preferred embodiment, the catalysts comprise less than 25 mole percent, preferably less than 10 mole percent, more preferably less than 1 mole percent, especially preferably less than 0.4 mole percent and most preferably less than 0.1 mole percent of noble metal atoms, based on the total number of metal atoms in the catalyst. The term "noble metals" refers in the context of the present invention to metals selected from the group consisting of ruthenium, rhodium, palladium, silver, rhenium, osmium, iridium, platinum, gold and mercury.

The number of metal atoms present in the catalyst can be measured by means of known elemental analysis methods, for example atomic absorption spectrometry (AAS), atomic emission spectrometry (AES), x-ray fluorescence analysis (XFA) or ICP-OES (Inductively Coupled Plasma Optical Emission Spectrometry).

The catalytically active metals can be used in the form of unsupported catalysts or on supports. Useful supports of this kind include, for example, carbon, such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The catalytically active metals can be used, for example, in the form of sponge catalysts, known as Raney catalysts. The Raney catalysts used are preferably Raney cobalt catalysts, Raney nickel catalysts and/or Raney copper catalysts.

Raney catalysts are prepared, for example, by treating an aluminum-metal alloy with concentrated sodium hydroxide solution, which leaches out the aluminum and forms a metallic sponge. The preparation of Raney catalysts is described, for example, in the Handbook of Heterogeneous Catalysis (M. S. Wainright in G. Ertl, H. Knözinger, J. Weitkamp (eds.), Handbook of Heterogeneous Catalysis, Vol. 1, Wiley-VCH, Weinheim, Germany 1997, page 64 ff.). Such catalysts are obtainable, for example, as Raney® catalysts from Grace or as Sponge Metal® catalysts from Johnson Matthey.

In a preferred embodiment, catalysts which are prepared by reduction of catalyst precursors are used in the process according to the invention.

The catalyst precursor comprises an active material which comprises one or more catalytically active components and optionally a support material.

The catalytically active components are oxygen compounds of the abovementioned metals, for example the metal oxides or hydroxides thereof, such as CoO, NiO, CuO and/or mixed oxides thereof.

In the context of this application, the term "catalytically active components" is used for abovementioned oxygen-metal compounds, but is not intended to imply that these oxygen compounds are already catalytically active per se. The catalytically active components generally have catalytic activity in the inventive conversion only on completion of reduction.

The catalyst precursors can be prepared by known processes, for example by precipitation, precipitative application or impregnation.

In a preferred embodiment, catalyst precursors which are prepared by impregnating support materials are used in the process according to the invention (impregnated catalyst precursors).

The support materials used in the impregnation can, for example, be used in the form of powders or shaped bodies, such as extrudates, tablets, spheres or rings. Support material suitable for fluidized bed reactors is preferably obtained by spray drying. Useful support materials include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary methods (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the corresponding catalytically active components or the doping elements, such as cobalt nitrate or cobalt chloride.

Thereafter, the impregnated support material is generally dried and optionally calcined. The impregnation can also be effected by the so-called "incipient wetness method", in which the support material is moistened with the impregnating solution up to a maximum of saturation according to its water absorption capacity. However, the impregnation can also be effected in supernatant solution.

In the case of multistage impregnation processes, it is appropriate to dry and if appropriate to calcine between individual impregnation steps. Multistage impregnation can be employed advantageously when the support material is to be contacted with metal salts in a relatively large amount.

To apply a plurality of metal components to the support material, the impregnation can be effected simultaneously with all metal salts or in any desired sequence of the individual metal salts.

In a further preferred embodiment, catalyst precursors are prepared by means of a coprecipitation of all of their components. To this end, in general, a soluble compound of the corresponding active component and of the doping elements, and optionally a soluble compound of a support material are admixed with a precipitant in a liquid while heating and while stirring until the precipitation is complete.

The liquid used is generally water.

Useful soluble compounds of the active components typically include the corresponding metal salts, such as the nitrates, sulfates, acetates or chlorides of the aforementioned metals.

The soluble compounds of a support material used are generally water-soluble compounds of Ti, Al, Zr, Si etc., for example the water-soluble nitrates, sulfates, acetates or chlorides of these elements.

The soluble compounds of the doping elements used are generally water-soluble compounds of the doping elements, for example the water-soluble nitrates, sulfates, acetates or chlorides of these elements.

Catalyst precursors can also be prepared by precipitative application.

Precipitative application is understood to mean a preparation method in which a sparingly soluble or insoluble support material is suspended in a liquid and then soluble compounds, such as soluble metal salts, of the appropriate metal oxides, are added, which are then precipitated onto the suspended support by adding a precipitant (for example, described in EP-A2-1 106 600, page 4, and A. B. Stiles, Catalyst Manufacture, Marcel Dekker, Inc., 1983, page 15).

Useful sparingly soluble or insoluble support materials include, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

Useful soluble compounds include the aforementioned soluble compounds of the active components or of the doping elements.

Typically, in the precipitation reactions, the soluble compounds are precipitated as sparingly soluble or insoluble basic salts by adding a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of 20 to 100° C., preferably 30 to 90° C., especially at 50 to 70° C.

The precipitates formed in the precipitation reactions are generally chemically inhomogeneous and generally comprise mixtures of the oxides, oxide hydrates, hydroxides, carbonates and/or hydrogencarbonates of the metals used. It may be found to be favorable for the filterability of the precipitates when they are aged, i.e. when they are left alone for a certain time after the precipitation, if appropriate under hot conditions or while passing air through.

The precipitates obtained by these precipitation processes are typically processed by washing, drying, calcining and conditioning them.

After washing, the precipitates are generally dried at 80 to 200° C., preferably 100 to 150° C., and then calcined.

The calcination is performed generally at temperatures between 300 and 800° C., preferably 350 to 600° C., especially at 450 to 550° C.

After the calcination, the pulverulent catalyst precursors obtained by precipitation reactions are typically conditioned.

The conditioning can be effected, for example, by adjusting the precipitation catalyst to a particular particle size by grinding.

After the grinding, the catalyst precursor obtained by precipitation reactions can be mixed with shaping assistants such as graphite or stearic acid, and processed further to shaped bodies.

Common processes for shaping are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff].

As described in the references cited, the process for shaping can provide shaped bodies in any three-dimensional shape, for example round, angular, elongated or the like, for example in the form of extrudates, tablets, granules, spheres, cylinders or grains. Common processes for shaping are, for example, extrusion, tableting, i.e. mechanical pressing, or pelletizing, i.e. compacting by circular and/or rotating motions. The conditioning or shaping is generally followed by a heat treatment. The temperatures in the heat treatment typically correspond to the temperatures in the calcination.

The catalyst precursors obtained by precipitation reactions comprise the catalytically active components in the form of a mixture of oxygen compounds thereof, i.e. especially as the oxides, mixed oxides and/or hydroxides. The catalyst precursors thus prepared can be stored as such.

Particular preference is given to catalyst precursors such as the oxide mixtures which are disclosed in EP-A-0636409 and which comprise, before the reduction with hydrogen, 55 to 98% by weight of Co, calculated as CoO, 0.2 to 15% by weight of phosphorus, calculated as $H_3PO_4$, 0.2 to 15% by weight of manganese, calculated as $MnO_2$, and 0.2 to 5.0% by weight of alkali metal, calculated as $M_2O$ (M=alkali metal), or oxide mixtures which are disclosed in EP-A-0742045 and which comprise, before the reduction with hydrogen, 55 to 98% by weight of Co, calculated as CoO, 0.2 to 15% by weight of phosphorus, calculated as $H_3PO_4$, 0.2 to 15% by weight of manganese, calculated as $MnO_2$, and 0.05 to 5% by weight of alkali metal, calculated as $M_2O$ (M=alkali metal), or oxide mixtures which are disclosed in EP-A-696572 and which comprise, before the reduction with hydrogen, 20 to 85% by weight of $ZrO_2$, 1 to 30% by weight of oxygen compounds of copper, calculated as CuO, 30 to 70% by weight of oxygen compounds of nickel, calculated as NiO, 0.1 to 5% by weight of oxygen compounds of molybdenum, calculated as $MoO_3$, and 0 to 10% by weight of oxygen compounds of aluminum and/or manganese, calculated as $Al_2O_3$ and $MnO_2$ respectively, for example the catalyst disclosed in loc. cit., page 8, with the composition of 31.5% by weight of $ZrO_2$, 50% by weight of NiO, 17% by weight of CuO and 1.5% by weight of $MoO_3$, or oxide mixtures which are disclosed in EP-A-963 975 and which comprise, before the reduction with hydrogen, 22 to 40% by weight of $ZrO_2$, 1 to 30% by weight of oxygen compounds of copper, calculated as CuO, 15 to 50% by weight of oxygen compounds of nickel, calculated as NiO, where the molar Ni:Cu ratio is greater than 1, 15 to 50% by weight of oxygen compounds of cobalt, calculated as CoO, 0 to 10% by weight of oxygen compounds of aluminum and/or manganese, calculated as $Al_2O_3$ and $MnO_2$ respectively, and no oxygen compounds of molybdenum, for example the catalyst A disclosed in loc. cit., page 17, with the composition of 33% by weight of Zr, calculated as $ZrO_2$, 28% by weight of Ni, calculated as NiO, 11% by weight of Cu, calculated as CuO and 28% by weight of Co, calculated as CoO, or The catalyst precursors thus obtained are generally reduced.

The reduction of the dry, generally pulverulent catalyst precursor can be performed at elevated temperature in a moving or stationary reduction oven.

The reducing agent used is typically hydrogen or a hydrogen-comprising gas.

The hydrogen is generally used in technical grade purity. The hydrogen can also be used in the form of a hydrogen-comprising gas, i.e. in admixtures with other inert gases, such as nitrogen, helium, neon, argon or carbon dioxide. The hydrogen stream can also be recycled into the reduction as cycle gas, optionally mixed with fresh hydrogen and optionally after removing water by condensation.

The catalyst precursor is preferably reduced in a reactor in which the shaped catalyst bodies are arranged as a fixed bed. The catalyst precursor is more preferably reduced in the same reactor in which the subsequent reaction of glycolaldehyde with diethanolamine and/or triethanolamine is effected.

In addition, the catalyst precursor can be reduced in a fluidized bed reactor in the fluidized bed.

The catalyst precursor is generally reduced at reduction temperatures of 50 to 600° C., especially of 100 to 500° C., more preferably of 150 to 400° C.

The partial hydrogen pressure is generally from 1 to 300 bar, especially from 1 to 200 bar, more preferably from 1 to 100 bar, where the pressure figures here and hereinafter are based on the absolute measured pressure.

The duration of the reduction is preferably 1 to 20 hours and more preferably 5 to 15 hours.

During the reduction, a solvent can be supplied in order to remove water of reaction which forms and/or in order, for example, to be able to heat the reactor more rapidly and/or to be able to better remove the heat during the reduction. In this case, the solvent can also be supplied in supercritical form.

Suitable solvents used may be the above-described solvents. Preferred solvents are water; ethers such as methyl tert-butyl ether, ethyl tert-butyl ether or tetrahydrofuran; or amides such as dimethylformamide or dimethylacetamide, or lactams such as N-methylpyrrolidone, N-ethylpyrrolidone, N-methylcaprolactam or N-ethylcaprolactam. Particular preference is given to water or tetrahydrofuran. Suitable solvents likewise include suitable mixtures.

The catalyst precursor can also be reduced in suspension, for example in a stirred autoclave. The temperatures are generally within a range from 50 to 300° C., especially from 100 to 250° C., more preferably from 120 to 200° C.

The reduction in suspension is generally performed at a partial hydrogen pressure of 1 to 300 bar, preferably from 10 to 250 bar, more preferably from 30 to 200 bar. Useful solvents include the aforementioned solvents.

The duration of the reduction in suspension is preferably 5 to 20 hours, more preferably 8 to 15 hours.

The catalyst can be handled under inert conditions after the reduction. The catalyst can preferably be handled and stored under an inert gas such as nitrogen, or under an inert liquid, for example an alcohol, water or the product of the particular reaction for which the catalyst is used. If appropriate, the catalyst must then be freed of the inert liquid before commencement of the actual reaction.

The storage of the catalyst under inert substances enables uncomplicated and safe handling and storage of the catalyst.

After the reduction, the catalyst can also be contacted with an oxygen-comprising gas stream such as air or a mixture of air with nitrogen. This affords a passivated catalyst. The passivated catalyst generally has a protective oxide layer. This protective oxide layer simplifies the handling and storage of the catalyst, such that, for example, the installation of the passivated catalyst into the reactor is simplified.

In a preferred embodiment, glycolaldehyde is contacted with an activated catalyst.

An activated catalyst can be prepared by reducing a catalyst precursor or by reducing a passivated catalyst.

In the context of the present invention, an activated catalyst is a catalyst which has been prepared by reducing a catalyst precursor and which has been handled under inert conditions during and after the reduction until the contacting with glycolaldehyde. In the context of the present invention, an activated catalyst is also a catalyst which has been prepared by reduction of a passivated catalyst and which has been handled under inert conditions during and after the reduction until the contacting with glycolaldehyde.

In such a catalyst, the metals are present partly in reduced form, and such a catalyst generally does not have a protective oxide layer.

As a measure of the activation of a catalyst is the degree of reduction.

In a preferred embodiment, the degree of reduction of the activated catalyst is 30% or more, preferably 50% or more, more preferably 75% or more and especially preferably 90% or more.

In a preferred embodiment, an activated catalyst which has been prepared by reducing a passivated catalyst has, after the activation, a degree of reduction which is at least 2%, preferably at least 3% and more preferably at least 4% above the degree of reduction of the passivated catalyst.

The degree of reduction is generally determined by "temperature-programmed reduction" (TPR).

Temperature-programmed reduction is effected by heating the sample of the catalyst precursor in a hydrogen/inert gas stream with a constant temperature increase per unit time. Preference is given to using an arrangement whose construction is based on the proposals by Monti and Baiker [D. A. M. Monti, A. Baiker, "Temperature-Programmed Reduction. Parametric Sensitivity and Estimation of Kinetic Parameters", J. Catal. 83 (1983) 323-335].

In this test setup, the pulverulent samples are introduced into a U-shaped glass tube as a loose bed between two glass wool plugs. The U-tube is within a ceramic tube oven. After installation into the TPR apparatus, the sample is first dried by heating it to 200° C. in an argon stream and holding it there for 30 minutes. Subsequently, it is cooled to 50° C. The sample is heated with a heating ramp of 5 K/min from 50° C. to an end temperature of 650° C. The sample temperature is measured in a thermocouple sleeve close to the bed and recorded at intervals of 2 s. A hydrogen/argon stream with 10% hydrogen is passed through the U-tube. The hydrogen content in the offgas is determined with a thermal conductivity detector. The hydrogen consumption is recorded as a function of temperature. By integration, the total $H_2$ consumption within the temperature range of interest is determined.

The degree of reduction RG can be calculated from the $H_2$ consumption by the following formula:

RG=100%−100%*[(measured hydrogen consumption of the catalyst sample (from TPR measurement))/ (theoretical hydrogen consumption of the fully oxidic catalyst which is calculated on the basis of the metal contents of the sample and reaction stoichiometry)]

In the calculation of the theoretical hydrogen consumption, the assumption is made that Ni, Cu and Co are present as NiO, CuO and CoO, and the aforementioned promoters are not present in reduced form. This is because, in the calculation of the degree of reduction, typically only those metal oxides which are reduced to the corresponding metals under the conditions of the TPR measurement are considered. For example, $ZrO_2$ is not reduced under the conditions of the TPR measurement, and so the Zr content is not taken into account in the determination of the degree of reduction.

The catalyst is preferably activated by reducing a catalyst precursor. The reduction of a catalyst precursor has already been described above.

A catalyst can also be activated by reducing a passivated catalyst. A passivated catalyst can be reduced as described above by treating a passivated catalyst with hydrogen or a hydrogen-comprising gas. The reduction conditions correspond generally to the reduction conditions employed in the reduction of the catalyst precursors. The activation generally eliminates the protective passivation layer.

An activated catalyst has to be handled under inert conditions during and after the activating reduction thereof.

The activated catalyst is preferably handled and stored under an inert gas, such as nitrogen, or under an inert liquid, for example an alcohol, water or the product of the particular reaction for which the catalyst is used. If appropriate, the activated catalyst then has to be freed of the inert liquid before commencement of the actual reaction.

In a preferred embodiment, the glycolaldehyde is contacted with the activated catalyst as described above.

The activated catalyst is preferably handled under inert conditions during and after the activation until the contacting. The glycolaldehyde is preferably also contacted with the activated catalyst under inert conditions, more preferably in the presence of hydrogen or a hydrogen-comprising gas.

In a preferred embodiment, the activated catalyst is contacted with glycolaldehyde in the reactor in which the catalyst has already been activated beforehand. According to the invention, the activated catalyst is handled under inert conditions during and after the activation until the contacting, preferably in the presence of hydrogen or a hydrogen-comprising gas. Alternatively, the activated catalyst, after it has been activated, can be stored in the presence of nitrogen or another suitable inert gas. To this end, the proportion of the inert gas in the hydrogen stream is generally increased gradually after the activation. Preference is also given to metering in the glycolaldehyde under inert conditions, preferably in the presence of hydrogen or of an inert gas.

In a further preferred embodiment, the activated catalyst is contacted with an inert liquid after the activation.

The activated catalyst is preferably contacted with an inert liquid by metering the inert liquid into the activated catalyst. The inventive conversion of glycolaldehyde preferably takes place in the same reactor in which the activation of the catalyst has also been undertaken.

The catalyst can, however, also be transferred together with the inert liquid into the reactor in which the contacting with glycolaldehyde is effected. The glycolaldehyde may already be present as an initial charge in the reactor, but it can also be metered into the reactor after the transfer of the catalyst. The contacting of the activated catalyst with glycolaldehyde preferably takes place under inert conditions, more preferably in the presence of hydrogen or of an inert gas.

In the process according to the invention, glycolaldehyde is reacted with monoethanolamine and/or diethanolamine.

Glycolaldehyde is commercially available and can be prepared, for example, by oxidation of ethylene glycol (see, for example, JP 3246248 and JP3279342). Glycolaldehyde is preferably synthesized by reaction of formaldehyde with carbon monoxide and hydrogen, as described, for example, in US2009012333, US2008081931, US2007249871, EP1697291, U.S. Pat. No. 4,503,260 and U.S. Pat. No. 4,322, 568.

In addition, monoethanolamine (MEOA) and/or diethanolamine (DEOA) is used in the process according to the invention.

MEOA and DEOA can be obtained by reacting ethylene oxide with ammonia. A detailed overview of the preparation process can be found in Ullmann's (Ullmann's Enzyklopädie der technischen Chemie, chapter "Ethanolamine and Propanolamine", Wiley-VCH, 2005).

In a preferred embodiment, MEOA which has been obtained without using ethylene oxide by reaction of glycolaldehyde with ammonia is used.

Glycolaldehyde is preferably reacted with ammonia in the presence of hydrogen and of a catalyst, the catalyst being activated by reducing a catalyst precursor or by reducing a passivated catalyst, which comprises effecting the reaction in the presence of a solvent and contacting the glycolaldehyde with the activated catalyst.

The catalysts used may preferably be those catalysts which have been activated as described above by reduction of a catalyst precursor or of a passivated catalyst.

The reaction of glycolaldehyde with ammonia in the presence of hydrogen preferably takes place in a solvent.

The solvent used may be any solvent which is inert under the reaction conditions and has a sufficient solubility for the reactants and reaction products.

Preferred solvents are water; ethers such as methyl tert-butyl ether, ethyl tert-butyl ether, dioxane or tetrahydrofuran (THF).

Useful solvents also include suitable mixtures of the solvents listed above.

Particularly preferred solvents are THF and water.

Particularly preferred solvents also include the reaction products of the inventive reaction of glycolaldehyde and the aminating agent.

The solvent can be used in a proportion of 5 to 95% by weight, preferably 20 to 70%, more preferably 30 to 60%, based in each case on the total weight of the reaction mixture, where the total weight of the reaction mixture is composed of the sum of the masses of the starting materials (glycolaldehyde and aminating agent) and solvents used in the process.

The ratio of ammonia to the glycolaldehyde used is typically within a range from 1:100 to 100:1, preferably 1:1 to 50:1 and more preferably 1:1 to 45:1.

The reaction is typically performed at a pressure of 1 to 500 bar, preferably 10 to 350 bar, more preferably at a pressure of 50 to 300 bar and most preferably 80 to 220 bar. The pressure is maintained or controlled generally via the metered addition of the hydrogen.

The reaction of glycolaldehyde with ammonia generally proceeds at temperatures of 15 to 350° C., preferably 50 to 250° C., more preferably 80 to 220° C.

In a particularly preferred embodiment, the ratio of ammonia to glycolaldehyde used is preferably 1:100 to 100:1, more preferably 1:1 to 50:1 and most preferably 1:1 to 45:1.

In this particularly preferred embodiment, the pressure is preferably 1 to 200 bar, more preferably 10 to 150 bar and most preferably 50 to 120 bar, and the temperature is preferably 20 to 300° C., more preferably 50 to 250° C. and most preferably 80 to 120° C. In this particular embodiment, the conversion of glycolaldehyde generally forms MEOA with high selectivity and yield.

The reaction of ammonia and glycolaldehyde to prepare monoethanolamine can be performed continuously, batchwise or semibatchwise. Typical reactors are, for example, high-pressure stirred tank reactors, autoclaves, fixed bed reactors, fluidized bed reactors, moving beds, circulating fluidized beds, salt bath reactors, plate heat exchangers as reactors, staged reactors with a plurality of stages with or without heat exchange and withdrawal/supply of substreams between the stages, in possible configurations as radial flow or axial flow reactors, continuous stirred tanks, bubble reactors, etc., the reactor suitable for the reaction conditions desired (such as temperature, pressure and residence time) being used in each case.

The process according to the invention is preferably performed in a high-pressure stirred tank reactor, fixed bed reactor or fluidized bed reactor.

In a particularly preferred embodiment, the process according to the invention is performed in one or more fixed bed reactors.

In a further particularly preferred embodiment, the conversion of glycolaldehyde is performed in a high-pressure stirred tank reactor.

The glycolaldehyde and ammonia can be introduced together into the reaction zone, for example as a premixed reactant stream, or separately. In the case of separate addition, the glycolaldehyde and the aminating agent can be added simultaneously, offset in time or successively to the reaction zone of the reactor.

The residence time in the case of performance in a batchwise process is generally 15 minutes to 72 hours, preferably 60 minutes to 24 hours, more preferably 2 hours to 10 hours.

In the case of performance in a continuous process, the catalyst hourly space velocity is generally in the range from 0.01 kg of glycolaldehyde/kg of catalyst/h to 3.0 kg of glycolaldehyde/kg of catalyst/h, preferably 0.05 kg of glycolaldehyde/kg of catalyst/h to 2.0 kg of glycolaldehyde/kg of catalyst/h and more preferably 0.1 kg of glycolaldehyde/kg of catalyst/h-1.5 kg of glycolaldehyde/kg of catalyst/h.

After the inventive reaction of glycolaldehyde with ammonia to give monoethanolamine, the monoethanolamine thus prepared can be isolated by processes known to those skilled in the art, for example by distillation.

In a further preferred embodiment, DEOA which has been obtained by reaction of glycolaldehyde with MEOA by means of the present process according to the invention is used in the process according to the invention.

A further feedstock used in the process according to the invention is hydrogen. The hydrogen is generally used in technical grade purity. The hydrogen can also be used in the form of a hydrogen-comprising gas, i.e. in mixtures with other inert gases, such as nitrogen, helium, neon, argon or carbon dioxide. The hydrogen-comprising gases used may, for example, be reformer offgases, refinery gases, etc., provided that these gases do not comprise any catalyst poisons for the catalysts used, for example CO. Preference is given, however, to using pure hydrogen or essentially pure hydrogen in the process, for example hydrogen with a content of more than 99% by weight of hydrogen, preferably more than 99.9% by weight of hydrogen, more preferably more than 99.99% by weight of hydrogen, especially more than 99.999% by weight of hydrogen.

The reaction of glycolaldehyde with MEOA and/or DEOA in the presence of hydrogen preferably takes place in a solvent.

The solvent may be any solvent which is inert under the reaction conditions and has a sufficient solubility for the reactants and reaction products.

Preferred solvents are water; ethers such as methyl tert-butyl ether, ethyl tert-butyl ether, dioxane or tetrahydrofuran (THF). Useful solvents also include suitable mixtures of the solvents listed above.

The solvent can be used in a proportion of 5 to 95% by weight, preferably 20 to 70%, more preferably 30 to 60%, based in each case on the total weight of the reaction mixture, where the total weight of the reaction mixture is composed of the sum of the masses of the starting materials (glycolaldehyde and MEOA and/or DEOA) and solvents used in the process.

The ratio of MEOA and DEOA to glycolaldehyde used is typically within a range of 1:100 to 100:1, preferably 1:1 to 50:1 and more preferably 1:1 to 45:1.

The reaction is typically performed at a pressure of 1 to 500 bar, preferably 10 to 350 bar, more preferably at a pressure of 50 to 300 bar and most preferably 80 to 200 bar. The pressure is maintained or controlled generally via the metered addition of the hydrogen.

The reaction of glycolaldehyde with MEOA and/or DEOA generally proceeds at temperatures of 15 to 350° C., preferably 50 to 250° C., more preferably 80 to 220° C.

The process according to the invention can be performed continuously, batchwise or semicontinuously.

Typical reactors are, for example, high-pressure stirred tank reactors, autoclaves, fixed bed reactors, fluidized bed reactors, moving beds, circulating fluidized beds, salt bath reactors, plate heat exchangers as reactors, staged reactors with a plurality of stages with or without heat exchange and removal/supply of substreams between the trays, in possible embodiments as radial flow or axial flow reactors, continuous stirred tanks, bubble reactors, etc., the reactor used in each case being that suitable for the desired reaction conditions (such as temperature, pressure and residence time).

The process according to the invention is preferably performed in a high-pressure stirred tank reactor, fixed bed reactor or fluidized bed reactor.

In a particularly preferred embodiment, the process according to the invention is performed in one or more fixed bed reactors.

In a further particularly preferred embodiment, glycolaldehyde is converted in a high-pressure stirred tank reactor.

The glycolaldehyde and MEOA and/or DEOA can be added together to the reaction zone of the reactor, for example as a premixed reactant stream, or separately. In the case of separate addition, the glycolaldehyde and MEOA and/or DEOA can be added to the reaction zone of the reactor simultaneously, offset in time or successively.

The residence time in the process according to the invention, in the case of performance in a batchwise process, is generally 15 minutes to 72 hours, preferably 60 minutes to 24 hours, more preferably 2 hours to 10 hours.

In the case of performance in a preferred continuous process, the catalyst hourly space velocity is generally in the range from 0.01 kg of glycolaldehyde/kg of catalyst/h to 3.0 kg of glycolaldehyde/kg of catalyst/h, preferably 0.05 kg of glycolaldehyde/kg of catalyst/h to 2.0 kg of glycolaldehyde/kg of catalyst/h and more preferably 0.1 kg of glycolaldehyde/kg of catalyst/h-1.5 kg of glycolaldehyde/kg of catalyst/h.

After the inventive reaction, the desired product can be isolated by processes known to those skilled in the art, for example by distillation.

The advantages of the present invention are that it has been possible to develop a process for preparing higher ethanolamines which enables a high conversion of glycolaldehyde and the formation of products, especially of DEOA and/or TEOA, in high yield and selectivity. Moreover, the conversion products are obtained in a high purity. These aims have been achieved under the premise that it is possible to use catalysts which are very substantially free of noble metals in the process according to the invention. The material costs of the process can therefore be lowered. This is because the use of noble metal catalysts leads to a great increase in the catalyst use costs, which has an adverse effect on the economic viability of the process. In the future, severe scarcity of raw materials can be anticipated, and so it can be expected that the prices of noble metals will rise further.

The process according to the invention is illustrated in detail with reference to the examples adduced below.

COMPARATIVE EXAMPLES

Preparation of the Catalyst Precursors

Catalyst Precursor a)

An aqueous solution of nickel nitrate, copper nitrate and zirconium acetate, which comprises 4.48% by weight of Ni (calculated as NiO), 1.52% by weight of Cu (calculated as CuO) and 2.82% by weight of Zr (calculated as $ZrO_2$), is coprecipitated in a stirred vessel in a constant stream with a 20% aqueous sodium carbonate solution at a temperature of 70° C., in such a way that the pH of 7.0 measured with a glass electrode is maintained. The resulting suspension is filtered and the filtercake is washed with demineralized water until the electrical conductivity of the filtrate is approx. 20 µS. Then a sufficient amount of ammonium heptamolybdate is incorporated into the still-moist filtercake that the oxide mixture specified below is obtained. Thereafter, the filtercake is dried at a temperature of 150° C. in a drying cabinet or a spray drier. The hydroxide-carbonate mixture obtained in this way is then heat treated at a temperature of 430 to 460° C. over a period of 4 hours. The catalyst precursor thus prepared has the composition of: 50% by weight of NiO, 17% by weight of CuO, 1.5% by weight of $MoO_3$ and 31.5% by weight of $ZrO_2$. The catalyst was mixed with 3% by weight of graphite and shaped to tablets.

Preparation of Catalyst Precursor (b):

An aqueous solution of nickel nitrate, cobalt nitrate, copper nitrate and zirconium acetate, which comprised 2.39% by weight of NiO, 2.39% by weight of CoO, 0.94% by weight of CuO and 2.82% by weight of $ZrO_2$, was coprecipitated in a stirred vessel in a constant stream with a 20% aqueous sodium carbonate solution at a temperature of 70° C., in such a way that the pH of 7.0 measured with a glass electrode was maintained. The resulting suspension was filtered and the filtercake was washed with demineralized water until the electrical conductivity of the filtrate was approx. 20 µS. Thereafter, the filtercake was dried at a temperature of 150° C. in a drying cabinet or a spray drier. The hydroxide-carbonate mixture obtained in this way was then heat treated at a temperature of 450 to 500° C. over a period of 4 hours. The catalyst precursor thus prepared had the composition of: 28% by weight of NiO, 28% by weight of CoO, 11% by weight of CuO and 33% by weight of $ZrO_2$. The catalyst precursor was mixed with 3% by weight of graphite and shaped to tablets.

Preparation of Catalyst Precursor (c):

By dissolving cobalt nitrate, manganese nitrate and phosphoric acid in water, a solution which comprises 10% by weight of cobalt, 0.55% by weight of manganese and 0.45% by weight of $H_3PO_4$ was prepared. By adding a 20% sodium carbonate solution, precipitation was effected at a temperature of 50° C. The precipitate formed was washed until no sodium or nitrate was detectable any longer in the washing water. The solid thus obtained was slurried with water and sprayed in a spray tower (inlet temperature=550° C.). The sprayed material was dried at 500° C., ground in a pan mill and shaped in an extruder to extrudates of diameter 4 mm. The extrudates were dried at 100 to 120° C. and then calcined at 650° C. for 1 h and then at 850° C. for 3 h. The catalyst precursor thus obtained comprised 90.4% by weight of cobalt, 5.1% by weight of manganese, 0.3% by weight of sodium and 3.1% by weight of phosphorus.

Preparation of Catalyst Precursor (d):

The catalyst precursor (d) was prepared according to Example 1A of EP-A-1317959, except without using iron (III) chloride.

Reduction and Passivation of the Catalyst Precursors

The oxidic tablets (catalyst precursors (a) and (b)) or extrudates (catalyst precursor (c)) or powder (catalyst precursor (d)) were reduced.

The reduction was performed at 280° C. at a heating rate of 3° C./minute. Reduction was effected first with 10% $H_2$ in $N_2$ for 50 minutes, then with 25% $H_2$ in $N_2$ for 20 minutes, then with 50% $H_2$ in $N_2$ for 10 minutes, then with 75% $H_2$ in $N_2$ for 10 minutes and finally with 100% $H_2$ for 3 hours. The percentages are each percentages by volume. The passivation of the reduced catalysts was performed at room temperature in dilute air (air in $N_2$ with an $O_2$ content of not more than 5% by volume).

Reactions of glycolaldehyde with MEOA:

Examples 1 TO 10

An electrically heated 160 ml autoclave (Hastelloy) with a mechanical magnet-coupled stirrer was initially charged with 3 g of commercial dimeric glycolaldehyde (50 mmol, calculated as the monomer) in the particular solvent (20 ml). Subsequently, the amount of the activated catalyst specified in Table 1 was added under an inert gas atmosphere, suspended in 10 ml of THF.

Before introduction into the autoclave, the passivated catalyst was activated as follows:

In Examples 1, 2 and 4, the passivated catalyst was reduced at 280° C. at a partial hydrogen pressure of 1 bar for 10 hours.

The degree of reduction was more than 30% in all cases.

In Examples 3 and 6 to 10, the passivated catalyst was reduced at 280° C. at a partial hydrogen pressure of 1 bar for 10 hours.

The degree of reduction was more than 30% in all cases.

In Example 5, the passivated catalyst was not activated.

Subsequently, MEOA, according to the molar ratio specified in Table 1 (MEOA:monomeric glycolaldehyde (GA)), was metered in and the mixture was heated to 100° C. On attainment of this temperature, a sufficient amount of hydrogen was injected that the reaction pressure specified was attained. During the reaction, the pressure was maintained by supplying further hydrogen, and the consumption was measured. In all cases, stirring was effected at 100° C. and the particular pressure for 8 h. The conversion was determined approximately with the aid of the hydrogen consumption. The reaction output was filtered off from the catalyst after 8 h, admixed with methanol and analyzed by GC (area percent).

The difference from 100% is unidentified secondary components.

Reactions of glycolaldehyde with DEOA:

Examples 11 TO 13

An electrically heated 160 ml autoclave (Hastelloy) with a mechanical magnet-coupled stirrer was initially charged with 3 g of commercial dimeric glycolaldehyde (50 mmol, calculated as the monomer) in the particular solvent (20 ml). Subsequently, the amount of the activated catalyst specified in Table 1, suspended in 10 ml of THF, was added under an inert gas atmosphere.

Before introduction into the autoclave, the passivated catalyst was activated as follows:

In Example 11, the passivated catalyst was reduced at 280° C. at a partial hydrogen pressure of 1 bar for 10 hours.

The degree of reduction was more then 30% in all cases.

In Example 12, the passivated catalyst was reduced at 280° C. at a partial hydrogen pressure of 1 bar for 10 hours.

The degree of reduction was more than 30% in all cases.

In Example 13, the passivated catalyst was not activated (comparative example).

Subsequently, DEOA corresponding to the molar ratio specified in Table 1 (DEOA:monomeric glycolaldehyde (GA)), was metered in and the mixture was heated to 100° C. On attainment of this temperature, a sufficient amount of hydrogen was injected that the stated reaction pressure was attained. During the reaction, the pressure was maintained by supplying further hydrogen and the consumption was measured. In all cases, the mixture was stirred at 100° C. and the particular pressure for 8 h. The conversion was determined by approximation with the aid of the hydrogen consumption. The reaction output after 8 h was filtered off from the catalyst, admixed with methanol and analyzed by GC (area percent). Unidentified by-products make up the difference to 100%.

Determination of the Degree of Reduction:

The measurement was recorded on a Micromeritics RS 232, Autochem II chemisorption analyzer. The evaluation software used was the program Autochem II 2920.

The temperature-programmed reduction was effected by heating the sample of the catalyst precursor in a hydrogen/inert gas stream with a constant temperature increase per unit time. A setup whose construction is based on the proposals by Monti and Baiker [D. A. M. Monti, A. Baiker, "Temperature-Programmed Reduction. Parametric Sensitivity and Estimation of Kinetic Parameters", J. Catal. 83 (1983) 323-335] was used. The pulverulent samples were introduced into a U-shaped glass tube as a loose bed between two glass wool plugs. The U-tube is within a ceramic tube oven. After installation into the TPR apparatus, the sample was first dried by heating it to 200° C. in an argon stream and holding it there for 30 minutes. Subsequently, it was cooled to 50° C. The sample was heated with a heating ramp of 5 K/min from 50° C. to an end temperature of 650° C. The sample temperature was measured in a thermocouple sleeve close to the bed and recorded at intervals of 2 s. A hydrogen/argon stream with 10% hydrogen was passed through the U-tube. The hydrogen content in the offgas was determined with a thermal conductivity detector. The hydrogen consumption was recorded as a function of temperature. By integration, the total $H_2$ consumption within the temperature range of interest was determined.

The degree of reduction RG was calculated from the $H_2$ consumption by the following formula:

RG=100%−100%*[(measured hydrogen consumption of the catalyst sample (from TPR measurement))/(theoretical hydrogen consumption of the fully oxidic catalyst which is calculated on the basis of the metal contents of the sample and reaction stoichiometry)]

TABLE 1

Reaction of glycolaldehyde with MEOA or DEOA.

| Example | Catalyst | Amount of cat. [g] | Solvent | Temperature [° C.] | Pressure [bar] | Molar ratio of MEOA:GA | Conversion [%] | EDA [%] | MEG [%] | AEEA [%] | DEOA [%] | TEOA [%] |
|---|---|---|---|---|---|---|---|---|---|---|---|---|
| 1 | (a) | 0.50 | THF | 100 | 100 | 5 | >90 | 6.4 | 0.0 | 0.0 | 29.4 | 58.6 |
| 2 | (a) | 0.50 | THF | 100 | 100 | 1 | 70 | 4.5 | 0.7 | 0.0 | 56.2 | 24.2 |
| 3 | (c) | 0.50 | THF | 100 | 100 | 5 | >90 | 3.9 | 0.0 | 1.0 | 46.1 | 46.2 |
| 4 | (b) | 0.50 | THF | 100 | 100 | 5 | 70 | 5.4 | 0.0 | 1.4 | 47.2 | 43.3 |
| 5 | (d) | 0.23 | THF | 100 | 100 | 5 | 30 | 0.0 | 0.0 | 0.0 | 27.9 | 65.7 |
| 6 | (c) | 0.50 | THF | 100 | 100 | 1 | 90 | 1.6 | 1.86 | 0.00 | 70.7 | 19.0 |
| 7 | (c) | 0.50 | THF | 100 | 100 | 5 | 80 | 1.6 | 0.09 | 0.30 | 51.1 | 43.4 |
| 8 | (c) | 0.50 | THF | 100 | 100 | 10 | 80 | 0.9 | 0.00 | 0.30 | 33.6 | 62.6 |
| 9 | (c) | 0.50 | water | 90 (1 h) | 100 | 10 | >50 | n.d. | n.d. | n.d. | 12.5 | 79.4 |
| 10 | (c) | 0.50 | water | 80 (1 h) | 100 | 1 | >50 | n.d. | n.d. | n.d. | 47.2 | 14.8 |

TABLE 2

Reaction of glycolaldehyde with MEOA or DEOA

| Example | Catalyst | Amount of cat. [g] | Solvent | Temperature [° C.] | Pressure [bar] | Molar ratio of DEOA:GA | Conversion [%] | EDA [%] | MEG [%] | DEOA [%] | TEOA [%] |
|---|---|---|---|---|---|---|---|---|---|---|---|
| 11 | (a) | 0.50 | THF | 100 | 100 | 2 | 80 | 8.6 | 1.1 | 0.0 | 77.6 |
| 12 | (c) | 0.50 | THF | 100 | 100 | 2 | 70 | 0.0 | 0.0 | 0.0 | 88.3 |
| 13 | (d) | 0.50 | THF | 100 | 100 | 2 | 50 | 0.0 | 0.0 | 0.0 | 74.8 |

The invention claimed is:

1. A process for preparing ethanolamines comprising reacting glycolaldehyde with monoethanolamine and/or diethanolamine in the presence of a catalyst.

2. The process of claim 1, wherein the catalyst is prepared by reducing a catalyst precursor.

3. The process of claim 1, wherein the catalytically active component of said catalyst is an oxygen compound of Ni, Co and/or Cu.

4. The process of claim 1, wherein the catalyst used comprises less than 0.4 mole percent of noble metal atoms selected from the group consisting of ruthenium, rhodium, palladium, silver, rhenium, osmium, iridium, platinum, gold, and mercury.

5. The process of claim 1, wherein the reaction is performed at a temperature of from 15 to 350° C.

6. The process of claim 1, wherein the reaction is performed at a pressure of from 10 to 350 bar.

7. The process of claim 1, wherein the reaction is performed in the presence of a solvent.

8. The process of claim 2, wherein the catalyst is activated and the glycolaldehyde is contacted with the activated catalyst.

9. The process of claim 8, wherein the activated catalyst has a degree of reduction of 30% or more.

10. The process of claim 9, wherein the activated catalyst which has been prepared by reducing a passivated catalyst has, after the activation, a degree of reduction which is at least 2% greater than the degree of reduction of the passivated catalyst.

11. The process of claim 9, wherein the activated catalyst is handled under inert conditions during and after the reduction until being contacted with glycolaldehyde.

12. The process of claim 1, wherein the ethanolamines prepared are diethanolamine and/or triethanolamine.

13. The process of claim 1, wherein the monoethanolamine used and/or the diethanolamine used has been prepared by reacting glycolaldehyde with ammonia and/or monoethanolamine.

* * * * *